US010227628B2

(12) United States Patent
Moularat et al.

(10) Patent No.: US 10,227,628 B2
(45) Date of Patent: *Mar. 12, 2019

(54) DEVICE FOR DETECTING A FUNGAL CONTAMINATION

(71) Applicant: Centre Scientifique Et Technique Du Batiment, Champs sur Marne (FR)

(72) Inventors: Stephane Moularat, Lognes (FR); Yael Joblin, Sucy en Brie (FR); Enric Robine, Lagny sur Marne (FR)

(73) Assignee: CENTRE SCIENTIFIQUE ET TECHNIQUE DU BATIMENT, Champs sur Marne (FR)

( * ) Notice: Subject to any disclaimer, the term of this patent is extended or adjusted under 35 U.S.C. 154(b) by 10 days.

This patent is subject to a terminal disclaimer.

(21) Appl. No.: 13/892,939

(22) Filed: May 13, 2013

(65) Prior Publication Data

US 2013/0323781 A1    Dec. 5, 2013

Related U.S. Application Data

(63) Continuation-in-part of application No. PCT/FR2011/052720, filed on Nov. 22, 2011.

(30) Foreign Application Priority Data

Nov. 23, 2010  (FR) ..................... 10 59636

(51) Int. Cl.
| G01N 33/00 | (2006.01) |
| G01N 33/569 | (2006.01) |
| C12Q 1/04 | (2006.01) |
| G01N 30/02 | (2006.01) |
| G01N 30/08 | (2006.01) |

(52) U.S. Cl.
CPC ........... *C12Q 1/04* (2013.01); *G01N 33/0047* (2013.01); *G01N 33/0075* (2013.01); *G01N 33/56961* (2013.01); *G01N 33/0031* (2013.01); *G01N 2030/025* (2013.01); *G01N 2030/085* (2013.01)

(58) Field of Classification Search
CPC .. G01N 33/0031; G01N 1/405; G01N 29/022; G01N 2291/0426; G01N 2291/0256; G01N 2291/0423; G01N 29/036; G01N 27/126; G01N 2030/085; G01N 2291/0257; G01N 2030/025; G01N 33/0047; G01N 33/0075
See application file for complete search history.

(56) References Cited

U.S. PATENT DOCUMENTS

| 4,600,559 A * | 7/1986 | Hiatt | G01N 25/14 422/240 |
| 5,047,073 A * | 9/1991 | Stetter | B01D 53/30 95/8 |
| 8,127,593 B2 | 3/2012 | Moularat | |
| 2011/0023581 A1* | 2/2011 | Chou | B01D 53/261 73/23.42 |
| 2012/0270330 A1* | 10/2012 | Tao | G01N 29/022 436/140 |

FOREIGN PATENT DOCUMENTS

| FR | 2913501 | 9/2008 |
| WO | WO 2008/125770 | 10/2008 |

OTHER PUBLICATIONS

Anonymous: (BW) (CA-Electronic-Sensor) zNose, on 'Eye in the Kingdom of the Blind' for the Chemical World, Electronic Sensor Technology, ( Nov. 7, 2001) p. 1-2, URL:http://www.estcal.com/press_release/articles/zNose%20Eye%20for%20Blind_files/f_headline.htm.

I.A. Casalinuovo, et al., Experimental Use of a New Surface Acoustic Wave Sensor for the Rapid Identification of Bacteria and Yeasts, Letters in Applied Microbiology, ( 2006) vol. 42, No. 1, p. 24-29.

S. Hamilton , et al., Detection of Serplua Lacrymans Infestation with a Polypyrrole Sensor Array, Sensors and Actuators B, (2006) vol. 113, No. 2, p. 989-997.

Jonas Holme, Detection, Assessment and Evaluation of Mould in Buildings in Relation to Indoor Environment and Effects on Human Health, Norwegian Building Research Institute, Report From R&D Programme Climate 2000, Project Report 406, Oct. 2006, pp. FP, 1-40.

Y. Joblin, et al., Detection of Moulds by Volatile Organic Compounds: Application to Heritage Conservation, International Biodeterioration and Biodegradation (2010) vol. 64, No. 3, p. 210-217.

E.J. Staples, The zNose: A New Electronic Nose Using Acoustic Technology, The Journal of the Acoustical Society of America (2000) Paper No. 2aEA4, p. 1-8.

* cited by examiner

*Primary Examiner* — Jennifer Pitrak McDonald
*Assistant Examiner* — Qing Xu
(74) *Attorney, Agent, or Firm* — Duane Morris LLP; Thomas J. Kowalski; Deborah L. Lu

(57) ABSTRACT

The present invention relates to a device for detecting a fungal contamination in an internal environment, to the use thereof and also to a method for detecting a fungal contamination in an internal environment using such a device.

11 Claims, No Drawings

DEVICE FOR DETECTING A FUNGAL CONTAMINATION

CROSS-REFERENCE TO RELATED APPLICATIONS AND INCORPORATION BY REFERENCE

This application is a continuation-in-part of PCT/FR2011/052720, filed on Nov. 22, 2011, which published as WO/2012/069752 on May 31, 2012, claiming priority to FR 10 59636, filed on Nov. 23, 2010, the entireties of which are expressly incorporated by reference herein.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a device for detecting a fungal contamination in an internal environment, to the use thereof and also to a method for detecting a fungal contamination in an internal environment using such a device.

The term "internal environment" is intended to mean a confined space inside a building which is noncontinuously aerated. Examples of internal environments can be found in homes, museums, churches, cellars, historical monuments, administrative buildings, schools and hospitals.

BACKGROUND OF THE INVENTION

The presence of molds in internal environments is not without consequences in terms of health. Indeed, many studies have demonstrated the appearance of symptoms in occupants of premises containing molds, and also their role in the degradation both of the materials and of the structures that they colonize. Indeed, the enzymes and/or the acids produced by the fungi also cause deterioration of their support.

Techniques for detecting the presence of molds in internal environments based on the visual recognition of a fungal development, and the culturing of conidia taken from the air or from surfaces do not make it possible to effectively detect "hidden" contaminations nor to detect contaminations early enough to effectively prevent the deterioration of their supports. Indeed, this deterioration is generally already advanced when the contamination is detectable by visual recognition. Furthermore, the time taken to obtain an answer with these measuring techniques is lengthy since it is necessary to await the growth in the laboratory of the microorganisms sampled before being able to carry out the analysis. Consequently, there is, in particular for certain sensitive fields such as the preservation of artistic or historical works, a demand for a solution which allows early detection and continuous monitoring of fungal contaminations.

As soon as they start to develop, fungi give out volatile molecules (volatile organic compounds, VOCs) resulting either from their metabolism, or from the degradation of the material on which they develop by the enzymes or the acids that they produce. The VOCs diffuse through the walls and can be detected in the air even in the case of hidden contaminations. However, the VOCs present in an internal environment can also come from other sources, such as building materials, household products or alternatively human activity. The concentrations of VOCs of fungal origin, in particular at an early stage of contamination, prove to be relatively low compared with all the VOCs present in an internal environment.

Patent application FR 2913501 proposes a method for detecting a fungal contamination in an internal environment by determining a fungal contamination index based on the analysis of the VOCs present in the ambient air. This method makes it possible to detect a fungal development at an early stage of its development even in the case of a hidden contamination, but uses conventional methods of analysis, such as gas chromatography coupled to mass spectrometry. These methods require the collection of a sample that must be brought back to the laboratory where it will undergo lengthy concentration, separation and analysis steps. These steps for detecting a fungal contamination in an internal environment require the intervention of a qualified technician and prove to be relatively lengthy and expensive. These analysis techniques do not therefore allow a rapid and continuous measurement.

Chemical sensors are commonly used for continuously measuring organic pollutants. However, such sensors are not sufficiently sensitive to detect the concentration levels of VOCs given out during a fungal development, nor sufficiently selective to differentiate these VOCs of fungal origin from the other VOCs originating from other biological sources or from the building materials.

The solutions available to date do not therefore make it possible to meet the demand for early detection and for continuous monitoring of fungal contaminations.

SUMMARY OF THE INVENTION

Provided is a device for detecting a fungal contamination in an internal environment which allows for a rapid in situ analysis of the ambient air with a short measurement time, and therefore the continuous detection of contamination. The device of the invention also has the advantage of being able to be used without the intervention of a specialized technician.

Thus, the present invention relates to a device for detecting a fungal contamination in an internal environment comprising:
  a preconcentration module;
  a separation module comprising a chromatographic microcolumn; and
  a detection module comprising a matrix of sensors.

DETAILED DESCRIPTION

The presence or the absence of mold in an internal environment cannot be deduced from the detection of a single VOC of fungal origin. The present inventors have therefore designed a device which uses a principle of detection of a fungal contamination based on the detection of certain target VOCs. The device of the invention therefore makes it possible in particular to detect the presence or the absence of target VOCs chosen from a range of target VOCs that can result from the development of a fungal contamination. The target VOCs comprise in particular:
  (1) the VOCs which are given off independently of the fungal species and of their support and which are given off only by fungal species, such as 1-octen-3-ol, 1,3-octadiene and methyl 2-ethylhexanoate;

(2) the VOCs which are given off independently of the fungal species and of the support, but which can also have other biological origins, such as 2-methylfuran, 3-methylfuran, 3-methyl-1-butanol, 2-methyl-1-butanol and α-pinene;

(3) the VOCs which are given off according to the fungal species and/or the support, such as 2-heptene, dimethyl sulfide, 4-heptanone, 2(5H)-furanone, 3-heptanol and methoxybenzene.

The target VOCs can also comprise VOCs which do not belong to category (1), (2) or (3), but which are involved in the assessment of the presence of a fungal contamination, such as 2-ethylhexanol.

In one embodiment of the present invention, provided is a device for detecting a fungal contamination in an internal environment, comprising:

a preconcentration module;

a separation module comprising a chromatographic microcolumn; and a detection module comprising a matrix of sensors.

In another embodiment of the present invention, provided is a device for detecting a fungal contamination in an internal environment, wherein the preconcentration module comprises an adsorbent material.

In a further embodiment of the present invention, provided is a device for detecting a fungal contamination in an internal environment, wherein the microcolumn has a length between 1 and 50 m.

In a still another embodiment of the present invention, provided is a device for detecting a fungal contamination in an internal environment, wherein the matrix of sensors comprises at least one polymer having an affinity with the VOCs of fungal origin.

In another embodiment of the present invention, provided is a device for detecting a fungal contamination in an internal environment, wherein the separation module also comprises a system for selecting target VOCs (volatile organic compounds).

In a further embodiment of the present invention, provided is a method for detecting a fungal contamination in an internal environment which is implemented by the device as defined above and which comprises:

taking a sample of VOCs from the environment;

separating the VOCs sampled; and detecting the VOCs present.

In another embodiment of the present invention, provided is the method as provided above, comprising:

taking a sample of VOCs from the internal environment;

separating the VOCs sampled;

selecting target VOCs; and detecting the target VOCs present.

In still another embodiment of the present invention, provided is the method as provided above, wherein the target VOCs are chosen from the group consisting of 1-octen-3-ol, 1,3-octadiene, methyl 2-ethylhexanoate, 2-methylfuran, 3-methylfuran, 3-methyl-1-butanol, 2-methyl-1-butanol, α-pinene, 2-heptene, dimethyl sulfide, 4-heptanone, 2(5H)-furanone, 3-heptanol, methoxybenzene and 2-ethylhexanol, and mixtures thereof.

In a yet another embodiment of the present invention, provided is the method as provided above, wherein the determining of the fungal contamination is carried out continuously.

The preconcentration module of the device according to the invention makes it possible to concentrate the target VOCs present in the ambient air to a concentration detectable by the detection module. The concentration of the VOCs can be carried out by any method known to those skilled in the art, in particular accumulation on an adsorbent material. The preconcentration module therefore advantageously comprises an adsorbent material which allows the accumulation of the target VOCs. The structure of the adsorbent material typically has a form which makes it possible to optimize its specific surface area. Preferably, the adsorbent material is in the form of particles typically having a size of from 50 to 200 μm, a specific surface area of from 20 to 50 $m^2/g$, a porosity of from 1 to 5 $cm^3/g$ and an average pore size of from 50 to 500 nm. The adsorbent material is preferentially chosen from activated carbon, silica gel, zeolites and porous synthetic resins, such as those sold under the brand Tenax®, Carbograph® or Chromosorb®. The preconcentration module advantageously also comprises a heating system allowing the desorption of the VOCs adsorbed onto the adsorbent material.

According to one particular embodiment of the device of the invention, the preconcentration module comprises a micro-preconcentrator. Such a micro-preconcentrator typically has a working volume of from 0.1 to 1 $cm^3$, preferably from 0.1 to 0.5 $cm^3$ and more preferentially from 0.1 to 0.3 $cm^3$. The micro-preconcentrator consists of a substrate plate, such as a silicon wafer, on the surface of which are etched grooves which contain the adsorbent material. A second plate, made of a material identical to or different than the substrate (such as a glass plate), adhesively bonded to the surface of the etched substrate plate comprising the grooves, contains the micro-preconcentrator. The substrate plate typically has a surface area of from 5 to 20 $cm^2$. The grooves advantageously have a length of from 3 to 10 cm, a width of from 200 to 1000 μm, a depth of from 200 to 1000 μm and a cross section of from 0.04 to 1 $mm^2$. The cross section of the grooves can have various shapes, such as rectangular, semicircular or circular.

Advantageously, the preconcentration module also comprises a forced-circulation system which makes it possible to force the ambient air to pass through the preconcentration module.

The separation module comprises a chromatographic microcolumn which advantageously has a cross section of from 0.01 to 0.25 $mm^2$. The length of the microcolumn must also be chosen so as to optimize the separation of the VOCs. It is advantageously greater than 1 m, preferably between 1 and 50 m. The choice of a long length makes it possible to improve the efficiency of the column and therefore to obtain better VOC separation. The microcolumn comprises a stationary phase that those skilled in the art will be able to choose so as to optimize the VOC separation. Said stationary phase advantageously belongs to the polysiloxane family (for example, dimethylpolysiloxane (PDMS)). Various stationary phases can also be used. These phases can be branched hydrocarbons, polyethylene glycols and polypropylene glycols, polyesters, polyaryl ether sulfones, or else stationary phases with specific selectivities.

The microcolumn comprises, for example, a substrate plate, such as a silicon wafer, on the surface of which is etched a groove which contains the stationary phase. A second plate, made of a material identical to or different than the substrate (such as a glass plate), adhesively bonded onto the surface of the etched substrate plate comprising the groove, contains the microcolumn. The substrate plate typically has a surface area of from 5 to 20 $cm^2$. The groove advantageously has a length of more than 1 m, preferably from 1 to 50 m, a width of from 100 to 500 μm, a depth of from 100 to 500 µm and a cross section of from 0.01 to 0.25 mm². The cross section of the grooves can have various shapes, such as rectangular, semicircular or circular. The groove can be arranged in various ways so as to minimize the bulkiness and therefore the size of the structure, for example in parallel twists (coil).

According to another embodiment of the device of the invention, the separation module also comprises a system for selecting the target VOCs, preferably comprising a solenoid valve and a programmable unit for controlling said solenoid valve. This selection system is directly connected to the outlet of the microcolumn. The retention time, for a given stationary phase and a given microcolumn length, is specific for each VOC. Thus, if information is provided on the retention times of each target VOC, the programmable unit can be preprogrammed such that the selection system selectively directs the portions of eluate corresponding to the retention times of each target VOC to the detection module, the rest of the eluate being discharged from the analysis circuit. Said portions of eluate can be either conveyed one after the other to the detection module, as the elution is carried out, or stored and then conveyed together into the detection module.

The target VOCs, comprising mainly VOCs of fungal origin, have very low concentrations compared with the total concentrations of all the VOCs present in the ambient air. Thus, this selective separation of the target VOCs makes it possible to prevent the formation of a background noise and/or the phenomena of hysteresis and/or of saturation of the sensors of the detection module that would be prejudicial to the detection of the target VOCs.

The detection module of the device according to the invention comprises a matrix of sensors advantageously chosen from electrochemical sensors of polymer type or of metal oxide type. The sensors preferably comprise a layer of polymer or blend of polymers having an affinity with the VOCs of fungal origin. The polymer can be chosen from polypyrroles, polythiophenes and polyanilines, and derivatives thereof. In particular, the sensitivity of polydifluorene, of poly(3,4-ethylenedioxythiophene)/sodium poly(styrene sulfonate) (PEDOT-PSS), of polypyrrole/sodium octane sulfonate and of polypyrrole/lithium perchlorate to a fungal environment have been demonstrated.

VOCs can be categorized into various families depending on their chemical nature: aliphatic VOCs, alcohols, ketones, esters, ethers, aldehydes, aromatic VOCs, chlorinated VOCs, nitrogenous VOCs or sulfur-containing VOCs. Chemical sensors for detecting compounds having a predetermined functional group exist. Such sensors make it possible to detect and identify the presence of a VOC belonging to a predetermined family, but do not make it possible to differentiate VOCs belonging to one and the same family.

In one particular embodiment, the matrix of sensors comprises sensors specific to each VOC family. In this case, the response of the matrix of sensors makes it possible to come to a conclusion as to the presence or absence of a VOC in a given portion of eluate, but is not sufficient on its own to determine the nature of the VOC detected. On the other hand, the response of the matrix of sensors makes it possible to determine the family or families to which the detected VOC belongs, and knowledge of the retention time of the portion of eluate under consideration makes it possible to know which target VOC may be present in said portion of eluate. Thus, it is possible to deduce the presence or absence of each target VOC by combining the information provided by the retention time and the matrix of sensors.

In another embodiment, the matrix comprises a set of sensors making it possible to obtain an overall fingerprint specific to each target VOC. The term "overall fingerprint" is intended to mean the combination of the responses of the set of sensors of the matrix. In this case, although each sensor of the matrix is not specific to a single target VOC, the combined response of several sensors makes it possible to specifically identify each target VOC. Thus, it is possible to deduce the presence or absence of each target VOC from the information provided by the matrix of sensors.

In another embodiment, the matrix of sensors comprises sensors specific to each target VOC. In this case, the matrix of sensors comprises as many sensors as there are target VOCs, and the response of each specific sensor makes it possible to individually conclude as to the presence or absence of the target VOC for which it is specific.

Advantageously, the detection module also comprises a containment chamber which confines the matrix of sensors. This chamber enables the containment of the sensitive layers of the sensors in order to expose them only to the samples to be analyzed. Advantageously, the containment chamber is made of a material that gives off little or no VOCs under the analysis conditions, such as stainless steel or polytetrafluoroethylene (PTFE), in order to avoid contamination of the sample to be analyzed.

In one particular embodiment, the device of the invention also comprises an information processing module. Said module is capable of interpreting the signals emitted by each sensor and of deducing the presence or absence of each target VOC. Preferably, the information processing module determines the presence or absence of a fungal contamination. This determination can be carried out, for example, by calculating a fungal contamination index as defined in patent application FR 2913501.

The conventional detection and/or identification methods use complex equipment such as mass spectrometers, infrared spectrometers, flame ionization detectors or thermal conductivity detectors which are difficult to miniaturize. The originality of the device of the invention lies in the coupling of a chromatographic microcolumn with chemical sensors. This device has the advantage of being able to be miniaturized and of being able to be used without the intervention of a specialized technician.

The device of the invention therefore has an advantage with regard to its size and its autonomy, which makes it possible to considerably reduce the time interval between successive measurements and/or the measurement response time. The duration of a measurement with the device of the invention is typically from 10 to 180 min, preferably from 30 to 120 min. Such a device therefore offers the possibility of setting up an effective strategy for monitoring fungal contaminations with a short time interval between measurements. Thus, an alert procedure can be envisioned in order to search for and treat contaminations at the first stages of development thereof. Furthermore, systems for controlling ambient air, such as CMVs, can be servo-controlled by the device of the invention in order to prevent or limit fungal development.

The present invention also relates to a method for detecting a fungal contamination in an internal environment which is implemented by the device of the invention and which comprises:
  taking a sample of VOCs from the internal environment;
  separating the VOCs sampled; and
  detecting the VOCs present.

The method of the invention comprises taking a sample of VOCs from the internal environment. To do this, the device of the invention is placed in the internal environment and the sample is taken by contact between the preconcentration module and the ambient air. In a first alternative, the sample is taken by natural convection of the ambient air. The taking of the sample then lasts between 60 and 300 min. In a preferred alternative, the sample is taken by forced convection causing the ambient air to pass through the preconcentration module. The flow rate of the ambient air passing through the sampling module is, for example, from 10 to 1000 ml/min. The taking of the sample then lasts between 5 and 60 min. The sample is preferably taken by adsorption of the VOCs onto an adsorbent material. In this case, the method of the invention also comprises a step of desorption of the adsorbed VOCs. Said step is carried out by thermal desorption under conditions well known to those skilled in the art.

The method of the invention also comprises separating the VOCs sampled. The separating of the VOCs sampled is carried out by means of the separation module. In particular, the VOCs sampled are separated by elution on a chromatographic microcolumn. The optimum parameters for separation, such as the column temperature or the flow rate of the mobile phase, are determined according to techniques well known to those skilled in the art as a function of the geometry of the column, of the nature of the stationary phase and of the vector gas.

The method of the invention also comprises detecting the VOCs present. As the elution proceeds, the eluate is directed to the detection module, where the detection of the VOCs present is carried out by virtue of the analysis of the eluate by the matrix of sensors.

In one preferred embodiment, the method of the invention comprises:
    taking a sample of VOCs from the internal environment;
    separating the VOCs sampled;
    selecting the target VOCs; and
    detecting the target VOCs present.

In this embodiment of the method according to the invention, target VOCs are selected from among the VOCs sampled by the separation module. This step is carried out by the selection system during the elution of the sample on the chromatographic microcolumn. To do this, the following procedure is carried out. Each target VOC elutes at a known different rate for a given chromatographic system. A given retention time is therefore attributed to a target VOC. The selection system is programmed with these values. The selection system is then capable of selecting the portions of eluate having a retention time corresponding to the target VOCs. These portions of eluate are then selectively conveyed to the detection module. The portions of eluate not corresponding to the preprogrammed values are eliminated. Consequently, only the presence or absence of the target VOCs is detected by the detection module.

Since the rest of the eluate is discharged from the analysis circuit, this makes it possible to avoid the phenomena of hysteresis and/or of saturation of the sensors of the detection module that could cause the presence of non-target VOCs which generally have a concentration well above that of the VOCs of fungal origin.

The target VOCs are preferably chosen from the group consisting of 1-octen-3-ol, 1,3-octadiene, methyl 2-ethylhexanoate, 2-methylfuran, 3-methylfuran, 3-methyl-1-butanol, 2-methyl-1-butanol, α-pinene, 2-heptene, dimethyl sulfide, 4-heptanone, 2(5H)-furanone, 3-heptanol, methoxybenzene and 2-ethylhexanol, and mixtures thereof.

Advantageously, the method of the invention also comprises determining a fungal contamination index, for example using the method as defined in patent application FR 2913501.

The method according to the invention is preferably used continuously. Advantageously, the duration of a measurement cycle is from 10 to 180 min, preferably from 30 to 120 min.

The present invention also relates to the use of the device according to the invention for detecting a fungal contamination in an internal environment.

The device of the invention can also be used in an ambient-air control system, such as a CMV.

The following exemplary embodiments illustrate the present invention without in any way limiting the scope thereof.

EXAMPLES

Example 1

Realization of the Device

The preconcentration module comprises a micro-preconcentrator etched on a silicon wafer by means of a DRIE process. The micro-preconcentrator is composed of 20 grooves 6 cm long, with a rectangular cross section 500 μm in width and 400 μm in length, and has a working volume of 0.25 m². The grooves are filled with particles of resin based on 2,6-diphenyl oxide, sold under the name Tenax® TA having an average diameter of 120 μm, a specific surface area of 35 m²/g, a porosity of 2.4 cm³/g and an average pore size of 200 nm. The micro-preconcentrator is closed by a silicon wafer adhesively bonded onto the surface comprising the grooves of the first wafer.

A chromatographic microcolumn was etched on a silicon wafer by means of a DRIE process. The microcolumn is composed of a groove 5 m long, with a rectangular cross section 150 μm in width and 200 μm in length. The groove is arranged in the form of parallel twists (or coil) having bends in the form of an arc of a circle in order to avoid the formation of blind spots. A stationary phase of PDMS, polydimethylsiloxane (Sylgard® 184, Dow Corning), is present inside the microcolumn. The microcolumn is closed with a second silicon wafer adhesively bonded onto the surface comprising the groove of the first wafer.

The detection module comprises a matrix of sensors composed of 4 polymer sensors. The polymer sensors have an affinity with the VOCs of fungal origin (respectively, PEDOT-PSS, polypyrrole/sodium octane sulfonate, polypyrrole/lithium perchlorate and polydifluorene) deposited on interdigitated electrode pairs. The matrix of sensors is placed in a PTFE containment chamber.

The various components are connected to one another and to the circulation system via NanoPort™ connectors.

Example 2

Calibration of the Microcolumn

For the calibration, the matrix of sensors of the device of Example 1 was replaced with a mass spectrometer.

The experimental parameters of the chain of analysis are collated in Table 1.

TABLE 1

GC/MS characteristics

| Parameters | Analytical conditions |
| --- | --- |
| Thermal desorber | Turbomatrix ATD (Perkin Elmer) |
| Desorption temperature | 370° C. |
| Desorption flow rate | 50 ml/min nitrogen N50 |
| Desorption time | 15 min |
| Cold trap temperature (Tenax TA) | −30° C. |
| Injection temperature (40° C./s) | 300° C. |
| Transfer line temperature | 220° C. |
| Gas chromatograph/ mass spectrometer | Autosystem XL/Turbomass (Perkin Elmer) |
| Microcolumn | Sylgard 184 |
| Vector gas | Helium N60 |
| Constant pressure | 37.5 psi |
| Temperature cycle | 40° C. for 2 min |
| | 1° C./min. up to 41° C. |
| | Plateau of 2 min |
| | 0.3° C./min. up to 44° C. for 2 min |
| | 1° C./min. up to 47° C. |
| | Plateau of 2 min |
| Mass spectrometry parameters | Quadripole EI mode, scan (33-400) |

Samples of the target VOCs were passed through the microcolumn in order to determine the retention times of each target VOC.

The retention times of each target VOC are listed in Table 2.

TABLE 2

| Compound | Retention time (min) |
| --- | --- |
| 1-octen-3-ol | 4.7 |
| 1,3-octadiene | 1.6 |
| methyl 2-ethylhexanoate | 9.1 |
| 2-ethylhexanol | 5.7 |
| α-pinene | 2.7 |
| 2-methylfuran | 0.5 |
| 3-methylfuran | 0.5 |
| 3-methyl-1-butanol | 1.4 |
| 2-methyl-1-butanol | 1.4 |
| 2-heptene | 0.8 |
| 4-heptanone | 2.1 |
| 3-heptanol | 4.8 |
| methoxybenzene | 2.6 |

Example 3

Detection of a Fungal Contamination

The device of Example 1, comprising a matrix of sensors, was placed in various healthy internal environments or internal environments exhibiting a fungal contamination at various stages of development.

VOC samples were taken from the internal environment by forced convection of the ambient air through the preconcentration module at a flow rate of 100 ml/min for 15 minutes.

The experimental parameters regarding the microcolumn are identical to those of Example 2.

The total measurement time is 20 min.

The responses of the matrix of sensors made it possible to detect the presence or absence of target VOC, and a fungal contamination index as defined in patent application FR 2913501 could also be calculated.

Having thus described in detail preferred embodiments of the present invention, it is to be understood that the invention defined by the above embodiments is not to be limited to particular details set forth in the above description as many apparent variations thereof are possible without departing from the spirit or scope of the present invention.

The invention claimed is:

1. A device for detecting a fungal contamination based on the detection of target VOCs (volatile organic compounds) in an internal environment comprising:
    a preconcentration module;
    a separation module comprising a chromatographic microcolumn comprising an outlet; and
    a detection module comprising a matrix of sensors
    wherein the separation module further comprises a selector, said selector comprises a solenoid valve directly connected to the outlet of the chromatographic microcolumn and a programmable unit for controlling said solenoid valve, said programmable unit being preprogrammed such that the selector is configured to selectively direct portions of eluate corresponding to a retention time of each of the target VOCs from the chromatographic microcolumn to the detection module and discharges the rest of the eluate,
    wherein the preconcentration module comprises a micropreconcentrator consisting of a substrate plate on the surface of which are etched grooves which contain an adsorbent material, and
    wherein the etched grooves have a length of from 3 to 10 cm, a width of from 200 to 1000 µm, a depth of from 200 to 1000 µm and a cross section of from 0.04 to 1 mm$^2$.

2. The device as claimed in claim 1, wherein the chromatographic microcolumn has a length between 1 and 50 m.

3. The device as claimed in claim 1, wherein the matrix of sensors comprises at least one polymer having an affinity with target VOCs (volatile organic compounds) of fungal origin.

4. The device as claimed in claim 1, wherein the target VOCs (volatile organic compounds) are selected from the group consisting of 1-octen-3-ol, 1,3-octadiene, methyl 2-ethylhexanoate, 2-methylfuran, 3-methylfuran, 3-methyl-1-butanol, 2-methyl-1-butanol, α-pinene, 2-heptene, dimethyl sulfide, 4-heptanone, 2(5H)-furanone, 3-heptanol, methoxybenzene and 2-ethylhexanol, and mixtures thereof.

5. The device as claimed in claim 1, wherein the substrate plate has a surface area of from 5 to 20 cm$^2$.

6. The device as claimed in claim 1, wherein the cross section of the grooves has a rectangular, semicircular or circular shape.

7. The device as claimed in claim 1, wherein the preconcentration module further comprise a second plate adhesively bonded to the surface of substrate plate with the etched grooves.

8. A method for detecting a fungal contamination in an internal environment which is implemented by the device as defined in claim 1 and which comprises:
    taking a sample of VOCs from the environment;
    separating the VOCs sampled; and
    detecting the VOCs present.

9. A method for detecting a fungal contamination in an internal environment which is implemented by the device as defined in claim 1 and which comprises:
    taking a sample of VOCs from the internal environment;
    separating the VOCs sampled;
    selecting target VOCs; and
    detecting the target VOCs present.

10. The method as claimed in claim 9, wherein the target VOCs are chosen from the group consisting of 1-octen-3-ol, 1,3-octadiene, methyl 2-ethylhexanoate, 2-methylfuran, 3-methylfuran, 3-methyl-1-butanol, 2-methyl-1-butanol, α-pinene, 2-heptene, dimethyl sulfide, 4-heptanone, 2(5H)-furanone, 3-heptanol, methoxybenzene and 2-ethylhexanol, and mixtures thereof.

11. The method as claimed in claim 9, wherein the detecting of the target VOCs is carried out continuously.

* * * * *

UNITED STATES PATENT AND TRADEMARK OFFICE
CERTIFICATE OF CORRECTION

PATENT NO. : 10,227,628 B2
APPLICATION NO. : 13/892939
DATED : March 12, 2019
INVENTOR(S) : Stephane Moularat et al.

Page 1 of 1

It is certified that error appears in the above-identified patent and that said Letters Patent is hereby corrected as shown below:

On the Title Page

Item (73), Correct the Assignee's address as follows:
(73) Assignee: CENTRE SCIENTIFIQUE ET TECHNIQUE DU BATIMENT, Champs sur Marne (FR)

Signed and Sealed this
Twenty-fifth Day of February, 2020

Andrei Iancu
*Director of the United States Patent and Trademark Office*